US007214657B2

(12) United States Patent
Kream

(10) Patent No.: US 7,214,657 B2
(45) Date of Patent: May 8, 2007

(54) METHOD OF TRANSPORTING A CHIMERIC HYBRID MOLECULE ACROSS THE BLOOD BRAIN BARRIER

(75) Inventor: Richard M. Kream, Huntington, NY (US)

(73) Assignee: Chimeracom, LLC, New York, NY (US)

( * ) Notice: Subject to any disclaimer, the term of this patent is extended or adjusted under 35 U.S.C. 154(b) by 235 days.

(21) Appl. No.: 10/720,039

(22) Filed: Nov. 20, 2003

(65) Prior Publication Data

US 2004/0259786 A1 Dec. 23, 2004

Related U.S. Application Data

(62) Division of application No. 10/134,187, filed on Apr. 26, 2002, now Pat. No. 6,881,829.

(51) Int. Cl.
*A01N 37/18* (2006.01)
*A61K 38/00* (2006.01)
*C07K 1/00* (2006.01)
*C07K 14/00* (2006.01)
*C07K 17/00* (2006.01)

(52) U.S. Cl. .......................................... 514/2; 530/402
(58) Field of Classification Search ..................... None
See application file for complete search history.

(56) References Cited

U.S. PATENT DOCUMENTS

| 5,891,842 A | 4/1999 | Kream |
| 6,063,758 A | 5/2000 | Lappi et al. |
| 6,310,072 B1 | 10/2001 | Smith et al. |
| 6,759,520 B1* | 7/2004 | Carr et al. ................... 530/402 |
| 6,881,829 B2* | 4/2005 | Kream ........................ 530/402 |

FOREIGN PATENT DOCUMENTS

WO   WO 01/30371 A   5/2001

OTHER PUBLICATIONS

Wainer BH, et al. Science 176(4039):1143-1145, 1972.*
Reuler, et al., *The Chronic Pain Syndrone: Misconceptions & Management*, Ann Intern Med. 93:588-596 (1980).
Sriwatankul, et al, *Anaylsis of Narcotic Analgesic usage in the Treatment of Postoperative Pain*, JAMA 250:926-929 (1983).
Schechter, *Pain & Pain Control in Children*, Current Problems in Pediatrics 15 (1985).
Goodman & Gilman, *The Pharmacological Basis of Therapeutics* 511 (7th ed. 1985).
Foran, et al, *A substance P-opioid chimeric peptide as a unique nontolerance-forming analgesic*, 97 PNAS 13:7521-26 (2001).
Egelton, et al, *Transport of Opioid Peptides into the Central Nervous System*, J Pharm Sci 1998, 87(11):1433-39.
Borchard, *Optimizing oral absorption of peptides using prodrug strategies*, J Control Release 1999; 62(1-2):231-38.
Stain-Texier, *Elevated concentrations of morphine 6-beta-D-glucuronide in brain extracellular fluid despite low blood-brain barrier permeability*, Br J Pharmacol 1999; 128(4):917-24.

Merrifield, *Solid Phase Synthesis*, SCIENCE 232: 241-47 (1986).
Barany, et al, *Solid-phase peptide synthesis; a silver anniversary report*, Int'l J Peptide Protein Res 30:705-39 (1987).
Kent, *Chemical Synthesis of Peptides and Proteins*, Ann Rev Biochem 57:857-989 (1988).
Kaiser, et al, *Peptide & Protein Synthesis by Segment Synthesis-Condensation*, SCIENCE 243:187-98 (1989).
Kream, *Substance P markedly potentiates the antinocicpetive effects of morphine sulphate administered at the spinal level*, 90 PNAS 5564-68 (1993).
Masczynska, et al, *Alternative forms of interaction of substance P and opioids innocicpetice transmission*, Ltrs Peptide Sci 298, 5:395-98 (1998).
Masczynska, et al, *Dual Functional Interactions of Substance P Opioids in Nociceptive Transmission*, Analgesia 3:259-68 (1998).
Watson, et al, *Tissue Selectivity of Substance P Alkyl Esters Suggesting Multiple Receptors*, Euro J Pharmacol 87:77-84 (1983).
Sizheng, et al, *Opioid and neurokinin activities of substance P fragments and their analogs*, Euro J Pharmacol 193:209-15 (1991).
Lipkowski, et al, *An Approach to the Self Regulatory Mechanism of Substance P Actions*, 33 Life Sciences141-44 (1983).
Foran, et al, *Inhibition of Morphine tolerance Development by a Substance P-Opioid Peptide Chimera*, J Pharmacol & Ex Thera 295:3:1142-48 (2000).
Lipkowski, et al, *Opioid Peptide Analogues: Reconsideration as a Potentially New Generation of Analgesics*, Polish J Chem, 68:907 12 (1994).
Misterek, et al, *Spinal Co-Administration of Peptide Substnace P Antagonist Increases Antinociceptive Effect of the Opioid Peptide Biphalin*, 54 Life Sciences, 14:939-44 (1994).
Foran, et al., *Chimeric Peptide for the Treatment of Acute & Chronic Pain*, ANESTHESIOLOGY 91:3A:A944 (1999).
Langel, et al, *Design of chimieric peptide ligands to galanin receptors and substance P receptors*, Intl J Peptide & Protein Res 39:6:516-533 (1992).
Cavagnero, et al, *Delta opioid Receptor Selectivity Ligands*, 49 Life Sciences 495-503 (1991).
Carr, et al, *Mechanisms of Opioid Analgetic Actions*, 1 Principles & Practice of Anesthesiology, Ch 32 (1993).
Lipkowski, et al, Neuropeptides: Peptide and Nonpeptide Analogs, Peptides: Synthesis, Structures and Applications. 1995, pp. 287-320. Academic Press.

* cited by examiner

*Primary Examiner*—Robert S. Landsman

(57) ABSTRACT

The present invention provides a method of transporting a pharmacologically active peptide across the blood brain barrier by administering to a living subject a conjugate molecule of a general class of chimeric hybrid conjugate molecules capable of simultaneous activation of MOR and SPR receptors within the CNS that is intrinsically a function of this class of molecules to permeate the mammalian BBB as an intact chemical entity. Accordingly, the chemical and pharmacological integrity of each of the receptor activating domains functionally enables BBB transport of its covalently bonded reciprocal receptor activating domain. As such, the requirement for an intact chimeric hybrid conjugate molecule as the only viable transport vehicle for equivalent BBB transport of each of its MOR and SPR receptor activation domains distinguishes the present invention as novel and unknown to the literature of CNS analgesic and anti-abuse drugs.

4 Claims, 1 Drawing Sheet

METHOD OF TRANSPORTING A CHIMERIC HYBRID MOLECULE ACROSS THE BLOOD BRAIN BARRIER

CROSS-REFERENCE TO RELATED APPLICATIONS

This is a division of Ser. No. 10/134,187 now U.S. Pat. No. 6,881,829, filed Apr. 26, 2002, as to which Applicant elected a restriction of the invention as required by an Office Action mailed on Sep. 23, 2003.

STATE REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

A written Sequence Listing and a computer readable form of the sequence listing, consisting of one file named ChimericHybridAnalgesics.ST25.txt on one disk, are attached as Appendices.

BACKGROUND OF THE INVENTION

Field of the Invention

The present invention lies firmly within the fields of drug, bio-effective and body treating compositions, more specifically a method for transporting chimeric hybrid molecules across the blood brain barrier (BBB). The present invention will be especially useful for transporting analgesic molecules possessing complex chemical structures consisting of one or more functional domains across the BBB to achieve acute and chronic pain relief or pharmaceutical amelioration of pain-related pathophysiological conditions.

Description of the Prior Art

The present invention relates to transporting novel hybrid alkaloid/peptide chimeric molecules across the BBB through the use of an alkaloid moiety.

Transporting analgesic compounds across the BBB is useful for achieving efficacious analgesia. The relief of suffering due to pain is an important objective of clinical practice and for restoring quality to life and the ability to function normally to pain sufferers.

Pain represents an integrated, complex, perception of noxious stimuli originating from somatic elements such as arms and legs and/or from visceral organs such as heart and liver.

Mechanistically, acute pain signaling involves noxious stimulation of free nerve endings innervating somatic elements and/or visceral organs leading to the activation of different types of slowly-conducting afferent fibers and of the A delta and C classes, terminating in the dorsal sensory spinal cord. A significantly more complex etiology underlies the initiation and persistence of chronic pain syndromes. This involves initial damage to peripheral nerves innervating somatic and visceral fields, persistent immunological challenge by cytokines and inflammatory mediators, reorganization of spinal cord and brainstem relay systems, and higher cortical adaptation.

From an established pharmacological perspective, opioids remain the key agents of choice for treatment of a wide variety of acute and chronic pain states. The prototype opioid analgesic or painkiller is morphine. Morphine and morphine-related opioids produce their painkilling effects by profound pharmacological inhibition of neurons of the peripheral/sensory nervous system (PNS) and the central nervous system (CNS). The biochemical and cellular effects of morphine, including potent analgesia, are transduced through a membrane-associated G-protein designated the mu ($\mu$) opioid receptor (MOR), found in high concentrations within the PNS and CNS. In a prior invention (U.S. Pat. No. 5,891,842), I established a therapeutic procedure or treatment regimen for inducing or eliciting a markedly enhanced opioid-dependent analgesic response within a living subject. That treatment methodology employs the concurrent administration of two recognized, self-contradicting and physiologically antagonistic compounds, the opioid analgesic morphine sulfate and the tachykinin peptide substance P (SP), at individual concentrations that had been empirically shown to have either marginal or completely ineffectual pharmacological properties in vivo. Because noxiously challenged or damaged sensory nerves release a variety of excitatory chemical mediators, including SP, the tachykinin SP had been previously designated as a nociceptive or pain-producing peptide transmitter at the spinal level. Nevertheless, my research demonstrates that at prescribed low nanogram concentrations SP appears to be a potent regulator of opioid analgesia in vivo.

Despite this apparent contradiction and the previously demonstrated physiological antagonism between these compounds in their traditional formats and conventionally used concentrations, my novel treatment process demonstrated a synergistic relationship over a period of time, and that an effective and efficacious opioid-induced analgesia results within the living subject from the process.

Unfortunately, because my prior invention requires the concurrent administration of two different self-contradicting and physiologically antagonistic compounds, SP and morphine, it presents difficulties in successfully establishing and testing the appropriate concurrent dosages for efficacious and safe administration in humans, as reflected by FDA and NIH clinical testing guidelines. This includes differences in the ability of morphine and of SP to cross the BBB.

While morphine is the prototype opioid analgesic or painkiller, its complex alkaloid characteristics differ greatly from those of peptides, and SP is a peptide. In subsequent research, therefore, collaborators and I combined the active pharmacological domains of SP and the peptide endomorphin-2 into one chemical entity: a novel seven amino acid peptide chimera, designated ESP7. Repeated administration of the chimeric molecule into the rat spinal cord milieu produced analgesia mediated by the MOR without a loss of potency over a 5-day time course. Essentially, ESP7 represented a non-tolerance forming compound with future potential as a specialized spinal analgesic for control of acute and/or chronic pain. (Foran, et al., A Substance P-opioid chimeric peptide as a unique non-tolerance-forming analgesic, 97 Proceedings of the National Academy of Sciences 13 (2000))

Although ESP7 provided the advantage of a single analgesic molecule, it has several unfortunate disadvantages. Operationally, the peptide chemical nature of ESP7 restricts its effective dosage and time-effect relationship within the CNS due to significant metabolism in the blood stream. This is supported by collected pharmacological data indicating significant difficulties encountered by peptide drug candidates for crossing the mammalian BBB (Eggleton R D, Abbruscato T J, Thomas S A, Davis T P Transport of opioid peptides into the central nervous system. J Pharm Sci 1998; 87(11):1433–9).

Morphine is a relatively complex organic molecule, termed an alkaloid due to its positively charged nitrogen group, unlike the endogenous peptide endomorphin-2 which provided the analgesic moiety in ESP7. Morphine is a highly efficacious MOR-selective opioid analgesic and will cross the human BBB, as will its active metabolite morphine 6-glucuronide. (Stain-Texier F, Boschi G, Sandouk P, Scherrmann J M, Elevated concentration of morphine 6-beta-D-glucuronide in brain extracellular fluid despite low blood-brain barrier permeability. Br J Pharmacol 1999; 128(4): 917–24) SP, however, is a peptide. Chimeric hybrid molecules possessing an alkaloid moiety and a peptide moiety are unknown to the literature of analgesia and to clinical practice. Chimeric hybrid molecules possessing an alkaloid moiety to activate the human MOR and a peptide moiety to concurrently activate the human SP receptor (SPR) are unknown to the literature of analgesia and to clinical practice. Chimeric hybrid molecules comprised of one moiety with a chemically modified morphine molecule to activate the human MOR and another moiety with a SP fragment to activate the human SPR are unknown to the literature of analgesia and to clinical practice. The method of inhibiting the development of opioid tolerance using such chimeric hybrid molecules is unknown to the literature of analgesia and to clinical practice.

Another major challenge is to design a molecule that will cross the BBB and produce analgesia in a living subject, while inhibiting tolerance development and dependence formation. Peptides do not readily cross the BBB. To achieve the analgesic effects I envisioned, a chimeric compound that activates both an MOR and SPR must cross the BBB. Such a molecule should be structured in such a way as to activate simultaneously the MOR and SPR domains in the PNS and/or CNS. With respect to both morphine and SP, a variety of alkaloid morphine and SP peptide fragments can be synthesized, having potentially different pharmacological effects if bound to another moiety. No obvious method is known for the SP moiety to be cross-linked to a morphine alkaloid moiety in a fashion that the resulting molecule will allow simultaneous activation of both the MOR and SPR receptors. Chimeric hybrid molecules with a moiety comprised of a chemically modified morphine molecule to provide the method to transport active SP fragments across the mammalian blood brain barrier are unknown to the literature of analgesia and to clinical practice.

The novelty of the present invention is not predictable according to the teachings of Syvanen and coworkers Syvanen, S., Xie, R., Sahin, S. & Hammarlund-Udenaes, M. (2006) Pharmacokinetic consequences of active drug efflux at the blood-brain barrier. Pharm. Res. 23, 705–717) who studied influx and efflux process of morphine and morphine-glucuronides in relation to their BBB permeability properties and brain concentrations. Syvanen and coworkers teach that efficacious BBB permeation is determined by a combination of influx hindrance (a gatekeeper function in the luminal membrane that is functionally linked to P-glycoproptein activation) and efflux enhancement by transports that pick up molecules on one side of the luminal or abluminal membrane and release them on the other side. The facilitative method of BBB transport of morphine and morphine congeners by covalently bonded heterologous SPR activating domains as found in the structure of chimeric hybrid conjugate molecules is not predictable by the general principle of BBB permeation by morphine and morphine congeners codified by Syvanen and coworkers. Conversely, the facilitative method of BBB transport of SP fragments or non-peptide SPR activating domains by covalently bonded heterologous morphine, morphine congeners, and opioid peptide MOR activating domains as found in the structure of chimeric hybrid conjugate molecules is not predictable by the teachings of Syvanen and coworkers.

Presently there also are no analgesic opioid chimeras that have crossed the BBB to achieve effective analgesia for mammalian acute or chronic pain without significant tolerance development and dependence formation.

Objects and Advantages

I have invented novel and useful methods employing heretofore unknown morphine-SP hybrid chimeras, as I have described below. Several objects and advantages of my present invention are:

a. a method for transporting, across the BBB, a molecule that can be dosed to produce effective analgesia in a living subject, i.e., a mammal (an animal class which includes humans),while inhibiting tolerance development;
b. a method for transporting, across the BBB, a molecule that can be dosed to produce effective analgesia in a living subject while inhibiting dependence formation;
c. a method for transporting, across the BBB, a molecule that can be dosed to produce effective opioid analgesia and that can be administered through a variety of methods of clinical administration, including oral, systemic and epidural administration;
d. A method for transporting, across the BBB, a molecule that can be dosed to produce effective opioid analgesia without significant restriction on its effective dosage and time-effect relationship within the CNS due to metabolism in the blood stream;
e. a method for transporting, across the BBB, a molecule that can be dosed to yield effective opioid analgesia with a reduction in the likelihood of undesirable side effects;
f. a method for transporting, across the BBB, a molecule that can be dosed to produce effective opioid analgesia with a reduction in the likely severity of undesirable side effects that become manifested by the patient;
g. a method for transporting, across the BBB, an opioid analgesic that can be dosed for administration to children without undue tolerance development;
h. a method for transporting, across the BBB, an opioid analgesic that can be dosed for administration to children without undue dependence formation; and
i. a method for transporting, across the BBB, an opioid analgesic suitable for PCA in the treatment of chronic and/or acute pain.

Additional objects and advantages of my present invention are:

a. to provide a method for transporting a chimeric molecule across the BBB so as to treat pain with opioid analgesia and little or no opioid tolerance development;
b. to provide a method for transporting a chimeric molecule across the BBB so as to treat pain with opioid analgesia and little or no opioid dependence formation;
c. to provide a method for transporting a chimeric molecule across the BBB so as to treat pain with opioid analgesia with reduced likelihood of undesirable side effects;
d. to provide a method of transporting a chimeric molecule across the BBB so as to provide opioid analgesia for PCA for acute and/or chronic pain; and
e. to provide a method of transporting a chimeric molecule across the BBB so as to treat drug abuse by administering as a substitute for the abused drug an analgesic that elicits little or no tolerance development or dependency formation and thereafter adjusting the dosage as tolerance and/or dependence is modulated.

Still further objects and advantages will become apparent from a consideration of the following description of my invention.

BRIEF SUMMARY OF THE INVENTION

The basis of the present invention is the construction of a general class of chimeric hybrid conjugate molecules capable of simultaneous activation of MOR and SPR receptors within the CNS that is intrinsically a function of this class of molecules to permeate the mammalian BBB as an intact chemical entity. Accordingly, the chemical and pharmacological integrity of each of the receptor activating domains functionally enables BBB transport of its covalently bonded reciprocal receptor activating domain. As such, the requirement for an intact chimeric hybrid conjugate molecule as the only viable transport vehicle for equivalent BBB transport of each of its MOR and SPR receptor activation domains distinguishes the present invention as novel and unknown to the literature of CNS analgesic and anti-abuse drugs.

The existence of functionally active chimeric hybrid molecules, of internally differing chemical nature, combining MOR- and SPR- activating domains linked by a novel molecular hinge are unknown to the literature of analgesia and to clinical practice.

The invention provides a method for transporting the chimeric hybrid molecules across the BBB using pharmaceutical compositions including hybrid alkaloid chimeric molecules and a pharamceutically acceptable carrier useful for the treatment of pain. It represents methods of treating pain using novel hybrid alkaloid/peptide chimeric molecules containing an opioid and SP moiety designed to achieve coincident activation of populations of MORs and SPRs as a novel pain treatment without tolerance and dependence. The hybrid alkaloid/peptide analgesics may be administered systemically or more preferably, orally. Solubility, absorption, and penetration through the human BBB will be markedly enhanced due to the hybrophilic and alkaloid chemical properties of morphine and morphine congeners. The invention therefore provides novel methods for treating pain using chemically modified morphine, a morphine congener a related multi-ranged MOR-preferring non-peptide alkaloid to serve both as an opioid analgesic as well as a pharmaceutically acceptable carrier for SP peptide absorption and stability after systemic administration as well as penetration through the human BBB. In these novel attributes, the method of inhibiting opioid tolerance development using hybrid alkaloid chimeric molecules differs substantially from prior art including the use of peptide ESP7.

The method of transporting novel chimeric hybrid molecules across the BBB by using chimeric hybrid molecules that encompass three chemically disparate functional domains, i.e., a ringed alkaloid MOR-activation domain, a peptide SPR-activation domain, and a flexible organic acid hinge domain, is unknown to the preclinical and clinical literature of pain and analgesia.

A desired objective of the present invention is that it will transport a chimeric hybrid molecule across the BBB such that the hybrid alkaloid/peptide chimeric molecules can be administered to produce clinically efficacious opioid analgesia with little or no development of opioid tolerance. With little or not tolerance development, escalating dosages will not be required to achieve the same pain killing effect and opioid dependence formation and undesirable side effects associated with escalating opioid dosages will be avoided or markedly reduced.

Detailed descriptions of one or more embodiments of the invention are described below. The novelty of the invention, as amply described above, will be apparent from the detailed description of structure and synthesis and from the claims. In the specification and the appended claims, the singular forms include plural referents unless the context clearly dictates otherwise. All technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated herein by reference.

DETAILED DESCRIPTION OF THE INVENTION

Figure 1:
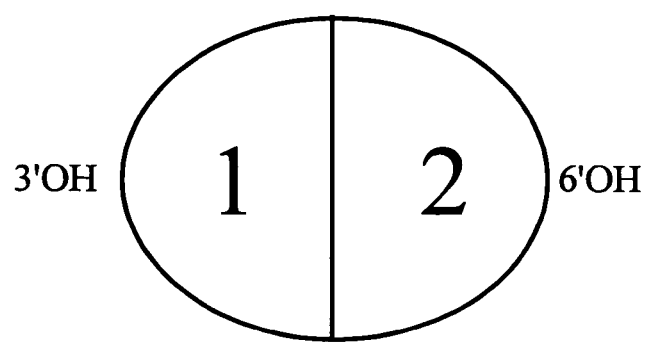
FIG. 1 illustrates schematically how a chimeric hybrid conjugate molecule is constructed of three linked components that that combine any non-peptide opioid with any active fragment of SP.
Figure 2:
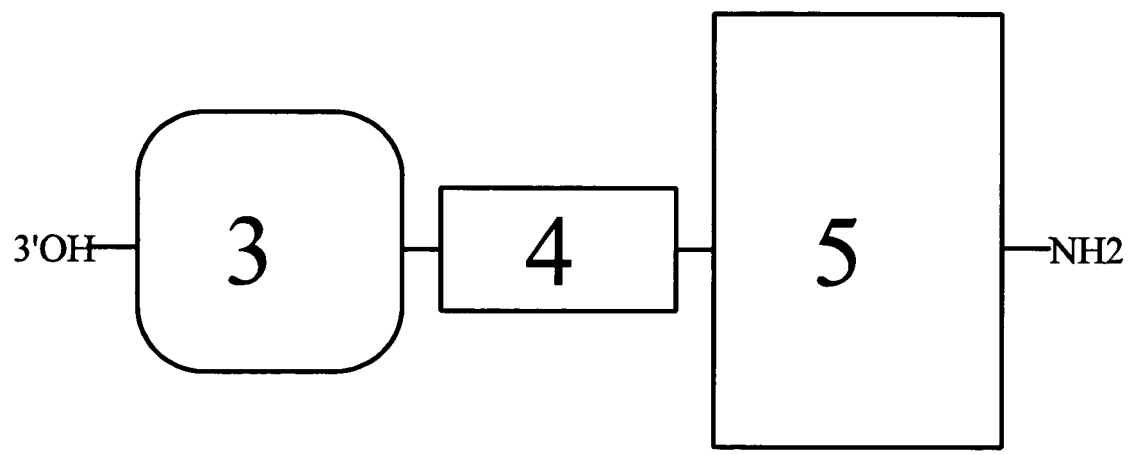
FIG. 2 illustrates schematically how a chimeric hybrid conjugate molecule is constructed of three linked components that combine any MOR-preferring opioid peptide with any non-peptide SPR activating domain.

Description—FIGS. 1 and 2 The present invention provides a method of transporting a chimeric hybrid molecule across the BBB so as to inhibit the development of opioid tolerance using hybrid alkaloid chimeric molecules having an MOR binding and activation moiety and an SPR binding and activation moiety. The hybrid alkaloid chimeric molecules are designed to cross the BBB. They can thus bind to and activate populations of MORs and SPRs located primarily within the human CNS, but also in the human PNS, involved in pain mediation and analgesic responses.

FIG. 1 depicts chimeric hybrid conjugate molecules that combine any non-peptide opioid with any active fragment of SP, or any peptide, for transport across the BBB that are constructed as capped, electrically neutral, linear sequences with the non-peptide opioid covalently bonded to the N-terminal end of the SP fragment through a 4–6 carbon molecule linker, or according to the teachings of Schiller (Schiller, P. W. (2005) Opioid peptide-derived analgesics. A.A.P.S. J. 7, E560–567) a more complex heterocyclic structure, and containing a neutral amide group at the C-terminal end of the SP fragment.

FIG. 1 depicts the construct of a linear chemical structure within the general class of chimeric hybrid conjugate molecules capable of simultaneous activation of MOR and SPR receptors within the CNS that contains a representative member of the morphinan, benzomorphan, or phenylpiperidine classes of non-peptide opioid alkaloid in covalent linkage to a representative member of the class of 4–6 carbon or more complex heterocyclic molecular linker in covalent linkage to a representative member of the class of biologically active fragments of SP that include SP 3-11, SP 4-11, SP 5-11, SP 6-11, and SP 7-11, and their chemically modified congeners.

Chimeric hybrid conjugate molecules that combine any non-peptide opioid with any active fragment of SP, or any peptide, for transport across the BBB are constructed as capped, electrically neutral, linear sequences with the non-peptide opioid covalently bonded to the N-terminal end of the SP fragment through a 4–6 carbon molecular linker, or according to the teachings of Schiller a more complex heterocyclic structure, and containing a neutral amide group at the C-terminal end of the SP fragment.

Representative candidate molecules chosen from the morphinan, benzomorphan, or phenylpiperidine classes of non-peptide opioid alkaloids, 4–6 carbon or more complex heterocyclic molecular linkers, and biologically active fragments of SP are listed in Table 1 and one of each may be covalently incorporated into the linear sequences of chimeric hybrid conjugate molecules according to guidelines gleaned from the teachings of Portoghese and coworkers [Bolognesi, M. L., Ojala, W. H., Gleason, W. B., Griffin, J. F., Farouz-Grant, F., Larson, D. L., Takemori, A. E. & Portoghese, P. S. (1996) Opioid antagonist activity of naltrexone-derived bivalent ligands: importance of a properly oriented molecular scaffold to guide "address" recognition at kappa opioid receptors. J. Med. Chem. 39, 1816–1822; Portoghese, P. S. (2001) From models to molecules: opioid receptor dimers, bivalent ligands, and selective opioid receptor probes. J. Med. Chem. 44:2259–69], Cascieri and Liang [Cascieri, M. A. & Liang, T. (1983) Characterization of the SPR in rat brain cortex membranes and the inhibition of radioligand binding by guanine nucleotides. J. Biol. Chem. 258, 5158–5164], and Mantyh and coworkers [Mantyh, P. W., Gates, T., Mantyh, C. R. & Maggio, J. E. (1989) Autoradiographic localization and characterization of tachykinin receptor binding sites in the rat brain and peripheral tissues. J. Neurosci. 9, 258–279.26] in reference to those of Liederer and coworkers [Liederer, B. M., Fuchs, J., Vander Velde, D., Siahaan, T. J. & Brochardt, R. T. (2006) Effects of amino acid chirality and the chemical linker on the cell permeation characteristics of cyclic prodrugs of opioid peptides. J Med Chem. 49, 1261–1270] and Schiller.

Table 1: Representative molecules covalently incorporated into the linear sequences of chimeric hybrid conjugate molecules that combine any non-peptide opioid with any active fragment of SP to produce opioid-dependent analgesia for acute and chronic pain indications without tolerance development via transport across the BBB.

Peptide sequences are listed under the appropriate SEQ. ID. NO.

1. Lys-Pro-Gln-Gln-Phe-Phe-Gly-Leu-Met-NH2
2. Pro-Gln-Gln-Phe-Phe-Gly-Leu-Met-NH2
3. Gln-Gln-Phe-Phe-Gly-Leu-Met-NH2
4. Gln-Phe-Phe-Gly-Leu-Met-NH2
5. Phe-Phe-Gly-Leu-Met-NH2
6. Lys-Pro-Gln-Gln-Phe-Phe-Gly-Leu-dNorLeu-NH2
7. Pro-Gln-Gln-Phe-Gly-Leu-dNorLeu-NH2
8. Lys-Pro-Gln-Gln-Phe-dTryp-Gly-Leu-dNorLeu-NH2
9. Pro-Gln-Gln-Phe-dTryp-Gly-Leu-dNorLeu-NH2

TABLE 1

| Non-peptide opioid alkaloids | Molecular linkers | Active fragments of substance P | SEQ. ID NO. |
|---|---|---|---|
| Morphine7,8-didehydro-4,5-epoxy-17-methylmorphinan-3,6-diol | Succinic acid ethane-1,2-dicarboxylic acid Gamma-hydroxy- | substance P 3–11 KPQQFFGLM-NH2 | 1. |

TABLE 1-continued

| Non-peptide opioid alkaloids | Molecular linkers | Active fragments of substance P | SEQ. ID NO. |
|---|---|---|---|
| Dihydromorphine7,8-dihydro-4,5-epoxy-17-methylmorphinan-3,6-diol | butyric acid d-glucuronic acid l-glucuronic acid oxaloacetic acid | substance P 4–11 PQQFFGLM-NH2 | 2. |
| Oxymorphone4,5-α-epxoy-14-hydroxy-17-methyl-morphinan-6-one | alpha ketoglutaric acid 2-Oxopentanedioic acid | substance P 5–11 QQFFGLM-NH2 | 3. |
| Oxycodone 4,5-α-epoxy-14-hydroxy-3-methoxy-17-methyl-morphinan-6-one | inositol cis-1,2,3,5-trans-4,6-cyclohexanehexol tetrahydroiso- | substance P 6–11 QFFGLM-NH2 | 4. |
| Hydrocodone4,5a-Epoxy-3-methoxy-17-methylmorphinan-6-one | quinoline-3-carboxylic acid | substance P 7–11 FFGLM-NH2 | 5. |
| Pentazocine 2-hydroxy-5,9-dimethyl-2-(3-methylbuten-2-yl)-6,7-benzomorphanium | | D-nor-leu substance P 3–11 KPQQFFGLd-nor-L-NH2 | 6. |
| Cyclazocine 2-cyclopropylmethyl-5,9-dimethyl-2'-hydroxy-6,7-benzomorphan | | D-nor-leu-substance P 4–11 PQQFFGLd-nor-L-NH2 | 7. |
| SufentanilN-[(4-(Methoxymethyl-1-(2-(2-thienyl)ethyl)-4-piperidinyl)]-N-phenylpropanamide | | D-nor-leu, D-tryp substance P 3–11 KPQQFdWGLd-nor-L-NH2 | 8. |
| Carfentanil4((1-oxopropyl)phenylamino)-1-(2-phenylethyl)-4-piperidinecarboxylic acid, methyl ester | | D-nor-leu, D-tryp substance P 4–11 PQQFdWGLd-nor-L-NH2 | 9. |

FIG. 2 depicts the construct of a linear chemical structure within the general class of chimeric hybrid conjugate molecules capable of simultaneous activation of MOR and SPR receptors within the CNS that contains a representative member of the class of MOR-preferring opioid peptide in covalent linkage to a representative member of the class of 4–6 carbon or more complex heterocyclic molecular linker in covalent linkage to a representative member of the class of non-peptide SPR activating domain.

Chimeric hybrid conjugate molecules that combine any MOR-preferring opioid peptide, or for that matter any peptide, with any non-peptide SPR activating domain for transport across the BBB are constructed as capped, electrically neutral, linear sequences with acetylation of the N-terminal of the opioid peptide that is covalently bonded at the C-terminal end to the non-peptide SPR activating domain through a 4–6 carbon molecular linker, or according to the teachings of Schiller a more complex heterocyclic structure.

Representative candidate molecules chosen from the class of MOR-preferring opioid peptides, 4–6 carbon or more complex heterocyclic molecular linkers, and non-peptide SPR activating molecules are listed in Table 2 and one of each may be covalently incorporated into the linear sequences of chimeric hybrid conjugate molecules according to guidelines gleaned from the teachings of Portoghese and coworkers, Cascieri and Liang and Mantyh and coworkers in reference to those of Liederer and coworkers and Schiller.

Table 2: Representative molecules covalently incorporated into the linear sequence of chimeric hybrid conjugate molecules that combine any MOR-preferring opioid peptide with any non-peptide SPR activating domain for production of opioid-dependent analgesia for acute and chronic pain indications without tolerance development via transport across the BBB. Peptide sequences are listed under the appropriate SEQ. ID NO.

10. Ac-Tyr-Gly-Gly-Phe-Met
11. Ac-Tyr-Gly-Gly-Phe-Met-Arg-Phe
12. Ac-Tyr-dAla-Gly-Phe-Met
13. Ac-Tyr-Gly-Gly-Phe-Leu
14. Ac-Tyr-Gly-Gly-Phe-Leu-Arg-Gly-Leu
15. Ac-Tyr-dAla-Gly-Phe-Leu
16. Ac-Tyr-Gly-Gly-Phe-Leu-Arg-Arg-Ile-Arg-Prop-Lys-Leu-Lys
17. Ac-Tyr-Pro-Phe-Phe

TABLE 2

| Mu opioid receptor-preferring opioid peptides | SEQ ID NO. | Molecular linkers | Non-peptide substance P receptor activating molecules |
|---|---|---|---|
| N-acetyl methionine enkephalin Ac-YGGFM | 10. | Succinic acid ethane-1,2-dicarboxylic acid | L-733,061 (partial agonist) |
| N-acetyl methionine enkephalin-Arg-Phe-Ac-YGGFMRF | 11. | Gamma-hydroxybutyric acid | (5S,6R)-6-alkyl-5-benzyloxy-2-piperidinone CP-99,994 (partial agonist) |
| N-acetyl, D-ala2, methionine enkephalin Ac-YdAGL\FM | 12. | d-glucuronic acid | (+)-(2S,3S)-3-(2-methoxybenzyl amino)-2-phenylpiperidine RP67580 (partial agonist) |
| N-acetyl leucine enkephalin AC-YGGFL | 13. | 1-glucuronic acid | |
| N-acetyl leucine enkephalin-Arg-Gly-Leu Ac-YGGFLRGL | 14. | oxaloacetic acid | [imino 1 (methoxy-2-phenyl)-2 ethyl]-2 diphenyl 7,7 perhydroisoin dolone-4 (3aR, 7aR) |
| N-acetyl,D-ala2, leucine enkephalin Ac-YdAGFL | 15. | alpha ketoglutaric acid 2-Oxopentanedioic acid | |
| N-acetyl dynorphin A (1–13) Ac-YGGFLRRIRPKLK | 16. | inositol cis-1,2,3,5-trans-4,6-cyclohexanehexol | |
| N-acetyl endomorphin 2 Ac-TPFF | 17. | tetrahydroiso quinoline-3-carboxylic acid | |

ADVANTAGES OF THE PRESENT INVENTION

The advantages of morphine as an analgesic that can cross the BBB are well known to the literature. The advantages of simultaneous activation of an MOR and SPR to modulate the activation of the MOR and to reduce or eliminate tolerance development and dependence formation are also known from the literature, such as a prior invention of mine (U.S. Pat. No. 5,891,842) and the work of colleagues of mine and I identified above relating to ESP7.

From the description above, a number of advantages of my method of inhibiting opioid tolerance development using chimeric hybrid analgesic molecules becomes evident:

a. the method will transport a chimeric hybrid molecule across the BBB so as to inhibit tolerance development while being dosed to provide morphine opioid analgesia;
b. the method will transport a chimeric hybrid molecule across the BBB so as to inhibit dependence formation while being dosed to provide morphine opioid analgesia;
c. the method can be used by means of administration of the molecules through a variety of methods of clinical administration, in addition to [[intrathecal]] epidural administration;
d. the method will not have the significant dosage and time-effect restrictions of peptides due to metabolism in the blood stream;
e. because of the modulation of an MOR by SPR activation, an escalating dosage typical of morphine is not required;
f. because the escalating dosage typical of morphine is not required, the likelihood and severity of undesirable effects associated with escalating morphine dosage will be reduced; and
f. the method can be used to administer a chimeric hybrid analgesic molecule as a substitute for an abused opioid drug and, because the molecule elicits little or no tolerance development or dependency formation, its dosage can thereafter be adjusted as tolerance and/or dependence is modulated.

Further advantages will becomes apparent to those skilled in the art.

Making My Invention.

In light of the work of Syvanen and coworkers cited above, the teachings of Liederer and coworkers provide us with guidelines by which to construct a general class of chimeric hybrid conjugate molecules that combine any non-peptide opioid with any active fragment of SP, or any peptide, for transport across the BBB. Liederer and coworkers teach that low BBB permeation is functionally linked to strong substrate activity for P-glycoprotein and efflux transporters in this biological barrier that is markedly enhanced for a variety of tested opioid peptide analogs sharing a common covalent cyclical structure. In contrast, capped, electrically neutral, linear derivatives of a variety of opioid peptide analogs with acetylation of the N-terminal and amidation of the C-terminal ends display efficacious permeation of the BBB via low substrate activity for P-glycoprotein and efflux transporters in this biological barrier.

Application of guidelines derived from the teachings of Liederer and coworkers in reference to the teachings of Syvanen and coworkers will enable any person skilled in the art to which it pertains to make and use the invention commensurate in scope with Claims 1–4, i.e., a general class of chimeric hybrid conjugate molecules capable of simultaneous activation of MOR and SPR receptors within the CNS. Chimeric hybrid conjugate molecules that combine any non-peptide opioid with any active fragment of SP, or any peptide, for transport across the BBB are constructed as capped, electrically neutral, linear sequences with the non-peptide opioid covalently bonded to the N-terminal end of the SP fragment through a 4–6 carbon molecular linker and containing a neutral amide group at the C-terminal end of the SP fragment. Chimeric hybrid conjugate molecules that combine any opioid peptide, or for that matter any peptide, with any non-peptide SPR activating domain for transport across the BBB are constructed as capped, electrically neutral, linear sequences with acetylation of the N-terminal of the opioid peptide that is covalently bonded at the C-terminal end to the non-peptide SPR activating domain through a 4–6 carbon molecular linker. Finally, the teachings of Schiller in reference to those of Syvanen and coworkers and Liederer and coworkers demonstrate a permissive chemical heterocyclic substitution in the internal domains of capped linear opioid peptide sequences that allow for efficacious BBB permeation, thereby providing validation for our specification indicating d-glucuronic acid, as a representative example of a closed-ring carbon structure, as an appropriate 6 carbon linker connecting linear MOR and SPR receptor activating domains within chimeric hybrid conjugate molecules.

The facilitate method of BBB transport of morphine and morphine congeners by covalently bonded heterologous SPR activating domains or conversely, of BBB transport of SP fragments or non-peptide SPR activating domains by covalently bonded heterologous morphine, morphine congeners, and opioid peptide MOR activating domains, requires maintenance of opioid and SP activities in chemically-modified structures of chimeric hybrid conjugate molecules. The teachings of Portoghese and coworkers in reference to those of Liederer and coworkers and Schiller provide specific indications for maintaining opioid activity following chemical modification of the multi-ringed non-peptide structures characteristic of morphinans, benzomorphans, and phenylpiperidines, as described for opioid peptide analogs. The construction of hybrid chimeric conjugates containing non-peptide opioids or chemically modified opioid peptide sequences are consistent with guidelines provided by Portoghese and coworkers, established authorities in the synthesis and structure-function relationships of non-peptide opioids, in reference to the teachings of Liederer and coworkers and Schiller and will enable any person skilled in the art to which it pertains to make and use the invention commensurate in scope with Claims 1–4, i.e., a general class of chimeric hybrid conjugate molecules capable of simultaneous activation of MOR and SPR receptors within the CNS.

In brief, the teachings of Portoghese and coworkers provide the following guidelines for preserving high affinity MOR activity for all non-peptide opioid domains found in the general class of chimeric hybrid conjugate molecules capable of simultaneous activation of MOR and SPR receptors within the CNS. Their teachings indicate that the A ring OH group at position 3 must be conserved during synthesis and/or conjugation to active SP fragments though a linker molecule. Consistent with the major body of published opioid research, conservation of the A ring OH group at position 3 is required for high affinity MOR activation. Thus, that A ring OH group at position 3 may be protected during synthesis or conjugation via covalent linkage to well recognized blocking groups that include Acetyl or T-butyl moieties. Following synthesis or construction of chimeric hybrid conjugates the Acetyl or T-butyl moieties are removed by gentle chemical treatment yielding non-peptide chemical moieties with a free A ring OH group at position 3.

The teachings of Portoghese and coworkers also indicate that the B ring OH group at position 6 of morphine or an equivalent position on the morphinan or benzomorphan multi-ringed structure is an appropriate site for chemical modification due to its location at a point distal to the obligate A ring OH group at position 3 of morphine or an equivalent position on the morphinan or benzomorphan multi-ringed structure. Chemical modification and linkage of the non-peptide opioid domain of molecules of the general class of chimeric hybrid conjugate molecules capable of simultaneous activation of MOR and SPR receptors within the CNS at a position spatially separated and distal to the obligate A ring OH group will permit binding in a sterically unhindered fashion to the MOR. The B ring OH group at position 6 of morphine or an equivalent position on the morphinan or benzomorphan multi-ringed structure may be further oxidized to a keto group with full retention of opioid activity. OH and keto groups are generally employed as chemical moieties capable of covalently linking discrete chemical entities through ester or ether chemistry. Finally, the teachings of Portoghese and coworkers indicate that multiple positions of the B ring, including the OH group at position 6 of morphine, or an equivalent position on the morphinan or benzomorphan multi-ringed structure, may be chemically modified without effecting opioid activity mediated by the obligate A ring OH group.

The construction of hybrid chimeric conjugates containing non-peptide opioids or chemically modified opioid peptide sequences are consistent with guidelines provided by Portoghese and coworkers, established authorities in the synthesis and structure-function relationships of non-peptide opioids, in reference to the teachings of Liederer and coworkers and Schiller and will enable any person skilled in the art to which it pertains to make and use the invention commensurate in scope with Claims 1–4, i.e., a general class of chimeric hybrid conjugate molecules capable of simultaneous activation of MOR and SP receptors within the CNS.

The teachings of Cascieri and Liang and Mantyh and coworkers provide specific indications for maintaining SP activity within the class of C-terminal fragments of SP. The rules provided by Cascieri and Liang and Mantyh and coworkers are considered to be general rules for evaluating bioactivities of fragments of SP by established investigators in SP research. According to their teachings and consistent with generally accepted formulations, all fragments of SP maintaining a fully intact C-terminal peptide domain equal to or greater than 5 amino acids have been determined to possess biological activity using a variety of testing paradigms. In the present invention, biologically active fragments of SP include SP 3-11, SP 4-11, SP 5-11, SP 6-11, and SP 7-11. All biologically active SP fragments contain only one free alpha amino group that is located at a site distal to SPR recognition domain and is utilized as the point of linkage of all active fragments of SP within the structure of the class of chimeric hybrid molecules described in the present invention. In sum, the teachings of Cascieri and Liang and Mantyh and coworkers in reference to the teachings of Portoghese and coworkers, Liederer and coworkers, and Schiller provide guidelines that will enable any person skilled in the art to which it pertains to make and use the invention commensurate in scope with Claims 1–4, i.e., a general class of chimeric hybrid conjugate molecules capable of simultaneous activation of MOR and SPR receptors within the CNS.

Prior to pharmacological testing, the novel chimeric hybrid molecules (such as those in Tables 1 and 2) are purified to over 99% purity by standard chromatographic techniques such as reverse-phase HPLC. This represents less than about 1% chemical precursors or non-peptide chemicals in the final preparations. The chemical structures of chimeric hybrid alkaloid/peptide molecules are confirmed by mass spectroscopic analysis. The chimeric hybrid molecules are then subjected to standard pharmacological testing.

Preclinically, a well-established method is used to assess the analgesic properties of the novel chimeric hybrid compounds, that being the tail flick test, which is administered to rats following parenteral or CNS administration. Additional tests of analgesic responsiveness include the paw withdrawal and hotplate tests, i.e., methods well-established as common in the art. Preclinical testing of analgesia and tolerance development is conducted by administration of the chimeric hybrid components over time and alternatively suing opioid and SP blockers in well-established analgesic testing methods. Further preclinical and clinical testing is conducted in conformity with governmental drug regulations.

Having made the chimeric hybrid molecules, they are administered to inhibit the development of opioid tolerance through means of clinical administration of analgesia well known to persons skilled in the art.

Using My Invention.

The present invention further provides a method of transporting a across the BBB chimeric hybrid molecules for treating a mammal for relief of pain by administering a pharmaceutical composition (as described above) in order to produce analgesia in the subject/patient. The invention is used by persons skilled in the art, as follows: Pharmaceutical compositions of the invention are formulated to be compatible with their intended routes of administration, e.g., parenteral, intrademal, subcutaneous, injectable, intravenous, oral, intradermal, subcutaneous, transdermal (topical), transmucosal, epidural and rectal administration.

Solutions or suspension suitable for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, sterile or bacteriostatic water, or phosphate buffered saline (PBS). In all cases, the compositions must be sterile and should be fluid to the extent that they are easily injectable by syringe. Proper fluidity may be maintained by the use of a coating such as lecithin, by the maintenance of the required particle size in the case of dispersion and by the use of surfactants. Preservation of chemical and pharmaceutical integrity is achieved by various antibacterial and antifungal agents: e.g., parabens, chlorobutanol, phenol, ascorbic acid, thimerosal, etc. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric hybrid molecules) in the required dosage in an appropriate solvent with one or a combination of ingredients enumerated above, as required, followed by filtered sterilization.

Oral compositions generally include an inert diluent or an edible carrier. They can be enclosed in gelatin capsules or compressed into tablets. For the purpose of oral therapeutic administration, the active compound can be incorporated with binders and used in the form of tablets, troches, or capsules. Pharmaceutical binding agents, and/or adjuvant material can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide.

Suitable intradermal, subcutaneous, transdermal (topical), and transmucosal formulations include: gels, creams, solutions, emulsions, suspensions, carbohydrate polymers, biodegradable matrices thereof, vapors, mists, aerosols and other inhalants, and skin patches. Rectal formulations also include suppositories and enemas.

Examples of suitable pharmaceutical carriers for the various forms of administration include any of the standard pharmaceutically accepted carriers known to those of ordinary skill in the art.

Examples of pharmaceutical carriers include but are not limited to buffered saline solution, water, emulsions, various wetting agents, tablets, coated tablets and capsules. Besides an effective amount of the compounds described in the present invention, pharmaceutical compositions may include suitable diluents, preservatives, solubilizers, emulsifiers, adjuvant and/or carriers. Examples of optimal ingredients which may be included in the pharmaceutical compositions of the present invention include antioxidants; low molecular weight polypeptides; proteins such as serum albumin, gelatin or immunoglobulins; amino acids such as glycine, chelating agents; sugar alcohols.

Because of the modulation of opioid tolerance and dependence, the invention may also be used for drug abuse intervention through administration of one or more embodiments of the chimeric hybrid analgesics which are the subjects of the invention in substitution for the drug to which the patient became tolerant and/or on which the patient became dependent.

Conclusions, Ramifications and Scope.

The reader thus will see that my invention provides a novel and useful method for transporting chimeric hybrid molecules across the BBB.

While my description contains many specifications, these should not be constructed as limitations on the scope of my invention, but rather as an exemplification of one or more of the preferred embodiments of my invention. Other variations are possible. Accordingly, the scope of my invention should be determined by the appended claims and their legal equivalents and not by the embodiments illustrated in the foregoing description.

I claim:

1. A method of transporting a pharmacologically active peptide across the blood brain barrier into the central nervous system of a living subject, by administration to said subject conjugate molecule comprising said peptide covalently linked to a non-peptide mu (μ) opioid receptor agonist, comprising:

a. Selecting a non-peptide mu (μ) opioid receptor agonist and a cross-linker, such that when the mu (μ) opioid receptor agonist is modified and covalently linked to the cross-linker and the cross-linker is covalently linked via a peptide bond to the pharmacologically active peptide, the cross-clinker will be able to flex such that the mu (μ) opioid opioid receptor agonist and the pharmacologically active peptide contemporaneously active their respective receptors;

b. Modifying the mu (μ) opioid receptor agonist such that it can be covalently attached to a flexible cross-linker, the covalent attachment of the modified mu (μ) opioid receptor agonist to the flexible hinge cross-linker, and the covalent attachment of the cross-linker via a peptide bond to the pharmacologically active peptide, to form a conjugate molecule; and c. Administering a pharmaceutical composition of said conjugate molecule to said living subject.

2. The method of claim 1 wherein the mu opioid receptor agonist is a pharmacologically active opioid.

3. The method of claim 2 wherein the opioid is a pharmacologically active form of morphine.

4. The method of claim 1 wherein the peptide is a pharmacologically active form of Substance P.

\* \* \* \* \*

SEQUENCE LISTING

```
<160> NUMBER OF SEQ ID NOS: 3

<210> SEQ ID NO 1
<211> LENGTH: 9
<212> TYPE: PRT
<213> ORGANISM: mammalian

<400> SEQUENCE: 1

Lys Pro Gln Gln Phe Phe Gly Leu Met
1               5

<210> SEQ ID NO 2
<211> LENGTH: 7
<212> TYPE: PRT
<213> ORGANISM: mammalian

<400> SEQUENCE: 2

Gln Gln Phe Phe Gly Leu Met
1               5

<210> SEQ ID NO 3
<211> LENGTH: 5
<212> TYPE: PRT
<213> ORGANISM: mammalian

<400> SEQUENCE: 3

Phe Phe Gly Leu Met
1               5
```